(12) United States Patent
Canestraro (10) Patent No.: US 12,343,307 B2
(45) Date of Patent: Jul. 1, 2025

(54) SUPPORT DEVICE FOR SUPPORTING A PLURALITY OF CONTAINERS FOR PHARMACEUTICAL USE TO BE HANDLED IN A PROCESSING LINE

(71) Applicant: NUOVA OMPI S.R.L. Unipersonale, Piombino Dese (IT)

(72) Inventor: Marco Canestraro, Carmignano di Brenta (IT)

(73) Assignee: NUOVA OMPI S.R.L. UNIPERSONALE, Piombino Dese (IT)

( * ) Notice: Subject to any disclaimer, the term of this patent is extended or adjusted under 35 U.S.C. 154(b) by 88 days.

(21) Appl. No.: 18/356,878

(22) Filed: Jul. 21, 2023

(65) Prior Publication Data

US 2024/0024196 A1    Jan. 25, 2024

(51) Int. Cl.
- *B65D 71/70* (2006.01)
- *A61J 1/16* (2023.01)
- *B65D 25/10* (2006.01)

(52) U.S. Cl.
CPC .............. *A61J 1/16* (2013.01); *B65D 25/108* (2013.01)

(58) Field of Classification Search
CPC ........ B65D 25/108; B65D 71/70; B65D 1/36; B65D 1/34; B01L 9/06; B01L 2200/025; A61J 1/16; B65B 43/54; A61M 5/008; A61M 5/002; A61M 2207/00; A61M 2209/06
USPC ....... 206/443, 563, 446; 220/507; 211/71.01
See application file for complete search history.

(56) References Cited

U.S. PATENT DOCUMENTS

| | | | |
|---|---|---|---|
| 8,800,800 B2 * | 8/2014 | Gerner | B65D 25/108 211/71.01 |
| 10,207,832 B2 | 2/2019 | Narvekar et al. | |
| 2009/0100802 A1 * | 4/2009 | Bush | A61M 5/002 53/434 |
| 2018/0126066 A1 | 5/2018 | Narvekar et al. | |
| 2020/0156840 A1 * | 5/2020 | Komann | B01L 9/06 |
| 2022/0227566 A1 | 7/2022 | Nau et al. | |

FOREIGN PATENT DOCUMENTS

WO         2014130349 A1    8/2014

* cited by examiner

*Primary Examiner* — King M Chu
(74) *Attorney, Agent, or Firm* — Husch Blackwell LLP (57) ABSTRACT

A support device for supporting a plurality of containers for pharmaceutical use to be handled in a processing line includes a plate having a plurality of first housing seats, wherein each first housing seat includes a first end edge defining an opening; and a base within each first housing seat, wherein the base includes at least one stacking element protruding above the first end edges of the first housing seats.

8 Claims, 9 Drawing Sheets

SUPPORT DEVICE FOR SUPPORTING A PLURALITY OF CONTAINERS FOR PHARMACEUTICAL USE TO BE HANDLED IN A PROCESSING LINE

CROSS REFERENCES

This application is a U.S. application claiming priority to Italian Application No. 102022000015636 filed on Jul. 25, 2022, the disclosure of which is incorporated herein by reference in its entirety.

TECHNICAL FIELD

The present disclosure relates to a support device for supporting a plurality of containers for pharmaceutical use to be handled in a processing line.

BACKGROUND

The support device of the present disclosure meets the definition of "nest" of ISO 21881:2019 standard.

Although explicit reference will be made in this description and the following claims to containers for pharmaceutical use, the support device of the disclosure is also suitable for supporting containers for medical, cosmetic or veterinary use.

For simplicity of discussion, in the present description all the containers that be supported by the support device of the disclosure are also indicated with the term "primary containers".

Non-limiting examples of primary containers are vials, ampoules, cartridges and syringes.

In the present description and in the appended figures specific reference will be made, as a non-limiting example of primary containers, to the cartridges.

As known, the primary containers are often handled in the processing lines by aggregating them into a secondary container called "nest".

In accordance with ISO 21881:2019 standard, the nest comprises a plate made of plastic material on which a plurality of housing seats configured to house primary containers are made. These housing seats are distributed in the plate according to a predetermined layout and are shaped so as to stably support the primary containers, keeping them separated from each other and thus avoiding possible mutual collisions.

It is also known to aggregate the primary containers into a so-called "nest and tub" configuration, in which the primary containers are placed inside the housing seats of a nest and the nest is in turn placed inside a tray so-called "tub". This configuration is particularly suitable for supporting and handling the primary containers during the various processing steps to which they are subjected along the processing line, such as washing, packaging, sterilization, filling, capping, crimping, freeze-drying, storage, manual or automated inspection operations, etc.

An example of nest is described in U.S. Pat. No. 10,207,832 B2.

The Applicant has noted that it is customary to stack multiple nests one over the other and handling the assembly defined by such stacked nests.

It is therefore advisable to provide the nests with appropriate measures to avoid relative movements between the various nests of the assembly (or stack) defined by them.

The technical problem underlying the present disclosure is to provide a support device that allows to stack thereon another support device avoiding relative displacements between the abovementioned two support devices after having been stacked.

SUMMARY

The present disclosure therefore relates to a support device for supporting a plurality of containers for pharmaceutical use to be handled in a processing line, comprising a plate having a plurality of first housing seats configured to house said containers, wherein each first housing seat comprises a first end edge defining an opening for inserting a respective container into the first housing seat and a base configured to support said container within the first housing seat, characterized in that it comprises at least one stacking element protruding above the first end edges of said first housing seats.

In the present description and in the appended claims, the terms "upper" and "lower", and similar terms such as "above" and/or "below" and/or "over" and/or "under", if present, are used with reference to the position taken by the support device during handling in the processing line of the containers for pharmaceutical use arranged therein.

The provision of the abovementioned stacking element makes it possible to obtain a stable assembly of two or more support devices stacked one over the other. In fact, said stacking element is configured to be stably housed in a respective recess provided on a lower surface of another support device, preventing said support devices, once they have been stacked one over the other, from being able to move with respect to each other.

The present invention can have at least one of the preferred features recited in the dependent claims and described hereinbelow, wherein each of these features can be provided individually or in combination with the other preferred features.

In a first preferred embodiment of the present invention, said at least one stacking element is connected to said plate.

Preferably, said at least one stacking element is made in a single piece with the plate.

Preferably, said first end edges protrude above the plate.

Preferably, the support device comprises four stacking elements.

In some embodiments, said four stacking elements are arranged near two opposite sides of the plate, more preferably with a substantially symmetrical arrangement with respect to a transverse centreline plane of the plate, with benefit for the stability of the assembly of stacked support devices thus formed.

Preferably, said at least one stacking element connects two adjacent first housing seats. This arrangement contributes to provide the plate, and therefore the support device of the invention, with a high stiffness or robustness.

Preferably, said two adjacent first housing seats are proximal to a perimeter edge of the plate. In this way the plate is strengthened precisely at the portions of the plate that are subjected to greater stresses during use. It is in fact at these portions that the support device is grasped for the handling thereof and the coupling of the support device with a tub.

Preferably, said at least one stacking element is shaped like a "V" or "I" or "C".

Preferably, said at least one stacking element is connected to a reinforcing rib arranged above said plate. In this way an advantageous strengthening of both the stacking element and, more generally, of the plate is obtained.

In a preferred embodiment of the invention, said plate comprises, on a lower surface thereof, at least one recess formed between two adjacent housing seats and configured to house a respective stacking element of a further support device. The support device can therefore be arranged both under another support device of the same type and over another support device of the same type, defining in both cases an assembly (or stack) of support devices that, thanks to the provision of stacking elements housed in respective recesses, is particularly stable.

In other embodiments, the stacking elements are arranged at at least two respective opposite vertices of the plate.

In another preferred embodiment of the invention, said plate comprises at least one second housing seat comprising a second end edge defining an opening for inserting a respective container into the second housing seat and which protrudes above the first end edges.

In this case the stacking element is defined by the above-mentioned second end edge.

In this case, preferably, each second housing seat comprises, at a lower end thereof, a base configured to support said container within said second housing seat and the plate comprises, on a lower surface thereof, a recess extended around the base of said second housing seat. Said recess is configured to house a second end edge of another support device identical to that of the invention, making also in this case a particularly stable assembly (or stack) of support devices.

In another innovative aspects thereof, the support device (hereinafter referred to as first support device) comprises a plate having a plurality of identical housing seats, each housing seat comprising a respective end edge defining an opening for inserting a respective container into the housing seat. In this case, a plurality of recesses is provided on a lower surface of the plate, each recess extending around a respective base of said housing seats.

In this case, the first support device can be placed above another support device of the same type (hereinafter referred to as "second support device") by inserting the end edges of the housing seats of the second support device into the recesses of the first support device, making also in this case a particularly stable assembly (or stack) of support devices.

These aspects are merely an illustrative aspect of the innumerable aspects associated with the present disclosure and should not be deemed as limiting in any manner. These and other aspects, features and advantages of the present disclosure will become apparent from the following detailed description when taken in conjunction with the referenced figures.

BRIEF DESCRIPTION OF THE DRAWINGS

Further characteristics and advantages of the present disclosure will become clearer from the following detailed description of preferred embodiments thereof, which is made with reference to the accompanying drawings and given for indicative and non-limiting purposes. In such drawings.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

In the following detailed description numerous specific details are set forth in order to provide a thorough understanding of the present disclosure. However, it will be understood by those skilled in the art that the present disclosure may be practiced without these specific details. For example, the present disclosure is not limited in scope to the particular type of industry application depicted in the figures. In other instances, well-known methods, procedures, and components have not been described in detail so as not to obscure the present disclosure.

The headings and sub-headings used herein are intended only for general organization of topics within the present disclosure and are not intended to limit the disclosure of the technology or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Detailed Description" section of this specification are hereby incorporated by reference in their entirety.

In FIGS. 1-4, a first embodiment of a support device for supporting a plurality of containers for pharmaceutical use (not shown) in accordance with the present disclosure is indicated overall with 10.

These containers are intended to be handled in a processing line (not shown).

Preferably, the abovementioned containers are cartridges.

The support device 10 comprises a body 15 having a substantially quadrangular shape. In the non-limiting example described herein, the body 15 is defined by a plate 20 having a substantially rectangular shape. Said plate 20 has four sides 21 and four vertices 22, which are preferably rounded.

The plate 20 of the support device 10 can be made by moulding plastic material, for example polypropylene.

The plate 20 comprises a flat surface which is perforated at a plurality of housing seats 30 configured to house respective cartridges.

The housing seats 30 are distributed in the plate 20 according to a predetermined layout and are shaped so as to stably support the cartridges, keeping them separated from each other and thus avoiding possible mutual collisions.

Figure 1:
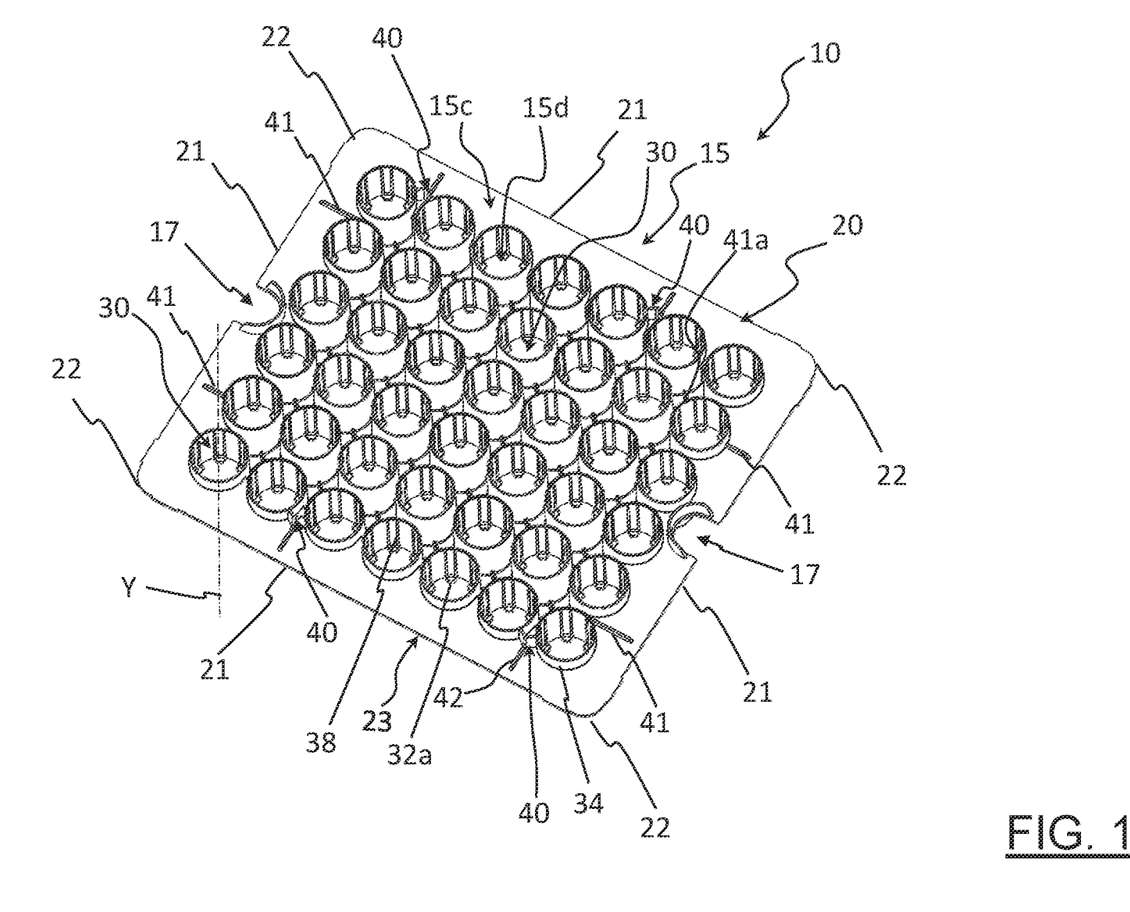
FIG. 1 is a schematic perspective top view of a first embodiment of a support device.

In the non-limiting example of FIGS. 1-4 the housing seats 30 are arranged in the plate 20 along a plurality of parallel rows (or columns) (FIG. 1). The housing seats 30 may however be arranged according to a staggered honeycomb or checkerboard configuration, like for example in FIGS. 7 to 10.

A plurality of housing seats 30 are adjacent to the sides 21 of the plate 20 and are hereinafter referred to as "perimeter housing seats 30", while another plurality of housing seats 30 are arranged in the plate 20 in a central position with respect to the perimeter housing seats 30 and are hereinafter referred to as "central housing seats 30".

The body 15, and hence the plate 20, has a perimeter portion 15c delimited externally by the four sides 21 and by the four vertices 22 of the plate 20, and a central portion 15d delimited by the perimeter portion 15c and comprising the perimeter housing seats 30 and the central housing seats 30. The four sides 21 and the four vertices 22 form a perimeter edge 23 of the plate 20.

Each cartridge has a substantially cylindrical shape and comprises a substantially circular open or closed base surface and, on the opposite side to the base surface, a top surface provided with a through opening configured to allow the filling of the cartridge with a predetermined amount of a pharmaceutical product, in the exemplary and non-limiting case of cartridges for pharmaceutical use.

The cartridges are typically made of glass or of a thermoplastic material.

After having placed the cartridges of a production batch in the housing seats 30 of the support device 10 with their top surface turned downwards, an organized assembly of cartridges is obtained, that allows the simultaneous handling and processing of all the cartridges of the production batch.

The cartridges, in fact, upon being placed in the housing seats 30 of the support device 10, are moved along the processing line by handling the support device 10. At least part of this handling is carried out after having inserted the support device 10 into a tub (not shown).

To this end, the perimeter portion 15c of the plate 20 comprises a pair of opposite through slots 17 configured to facilitate the insertion and the extraction of the support device 10 into/from the tub.

The tub has a substantially parallelepipedal or truncated-pyramidal shape and comprises a substantially flat bottom surface and four substantially flat side walls which are connected two by two by respective connecting walls.

An inner perimeter edge extends from the inner faces of the side walls and of the connecting walls inwardly in the tub. This inner perimeter edge defines an abutment surface on which the perimeter portion 15c of the plate 20 is intended to rest when the support device 10 is placed inside the tub. The inner perimeter edge may be replaced by a plurality of ribs extending from the inner faces of the side walls and/or connecting walls, each rib comprising a rest surface defining a respective abutment surface on which the perimeter portion 15c of the plate 20 is intended to be rested.

Once the cartridges of a production batch are inserted into the housing seats 30 of the support device 10 and the latter is inserted into the tub, an aggregation configuration of the cartridges known as "nest and tub" is made, in which the support device 10 is the "nest" and the tub is the "tub".

As shown for example in FIG. 3, the housing seats 30 extend on opposite sides of the plate 20 between a lower surface 15a arranged below the plate 20 and an upper surface 15b that, in the specific example shown in the accompanying drawings, is arranged above the plate 20 but that in other embodiments can be defined by the upper face of the plate 20.

The lower surface 15a is substantially flat and is defined at lower ends 31a of the housing seats 30.

The upper surface 15b is also substantially flat and is defined at the upper ends 31b of the housing seats 30.

Each of the housing seats 30 comprises, at the lower end thereof 31a, a base 32 having a through opening 33 and, at the upper end thereof 31b, an end edge 35 defining a through opening 36 configured to allow the insertion and the extraction of a respective cartridge. The end edges 35 of the housing seats 30 project above the plate 20, all at the same height.

The base 32 has a predetermined thickness measured between a lower face of the base 32 that is configured to rest on a substantially horizontal operating surface of the processing line and that lies on the abovementioned lower surface 15a and an upper face of the base 32 that is configured to support the cartridge.

Each housing seat 30 further comprises a side wall 34 which, in the non-limiting example of FIGS. 1-4, is substantially cylindrical and delimits a substantially cylindrical space configured to receive the cartridge.

The side wall 34 extends starting from the base 32 up to the upper surface 15b of the plate 20 along a longitudinal axis Y that is substantially orthogonal to the abovementioned flat surface of the plate 20.

Figure 3:
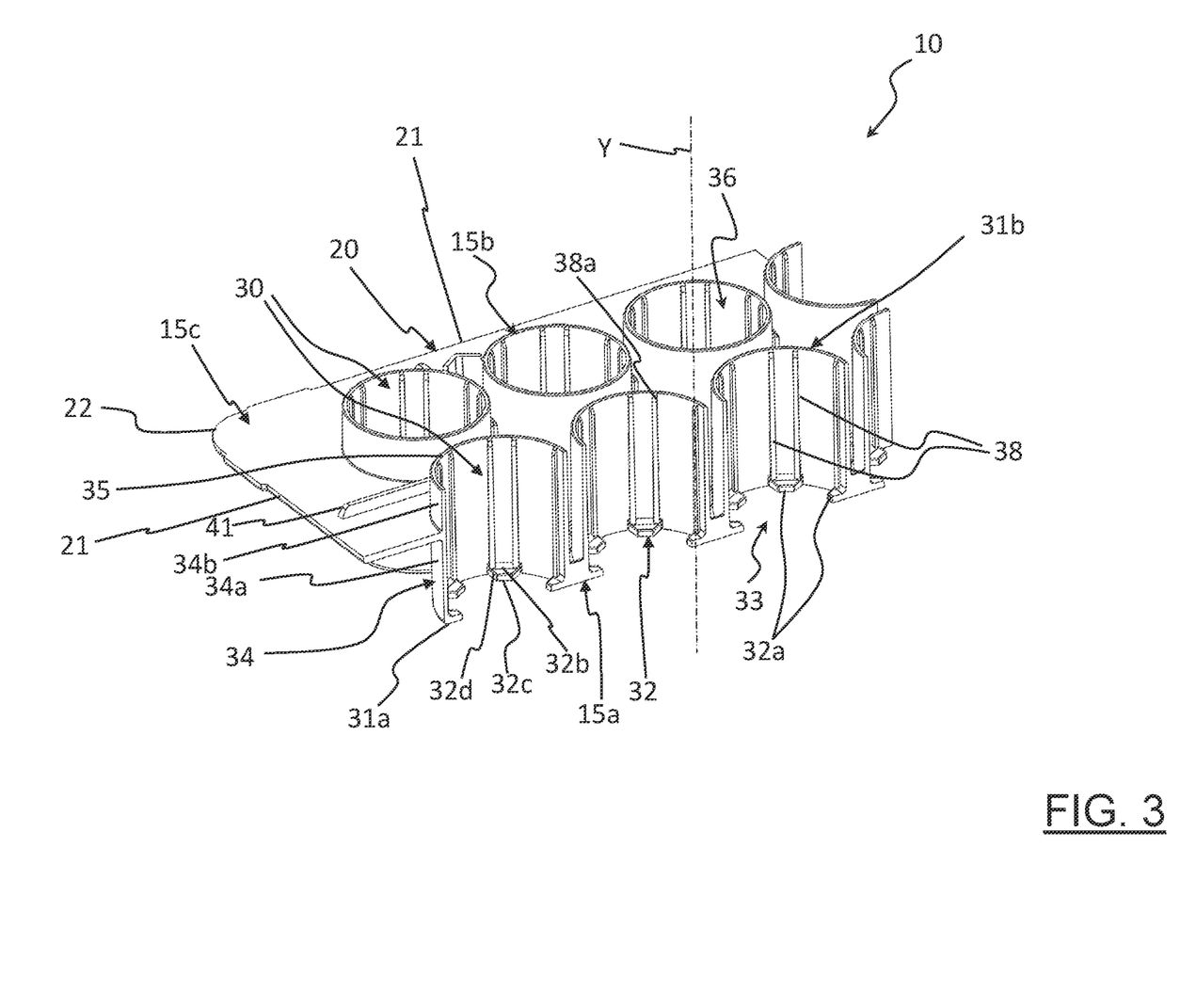
FIG. 3 is a schematic perspective view, in section and on an enlarged scale of a portion of the support device of FIG. 1.
Figure 4:
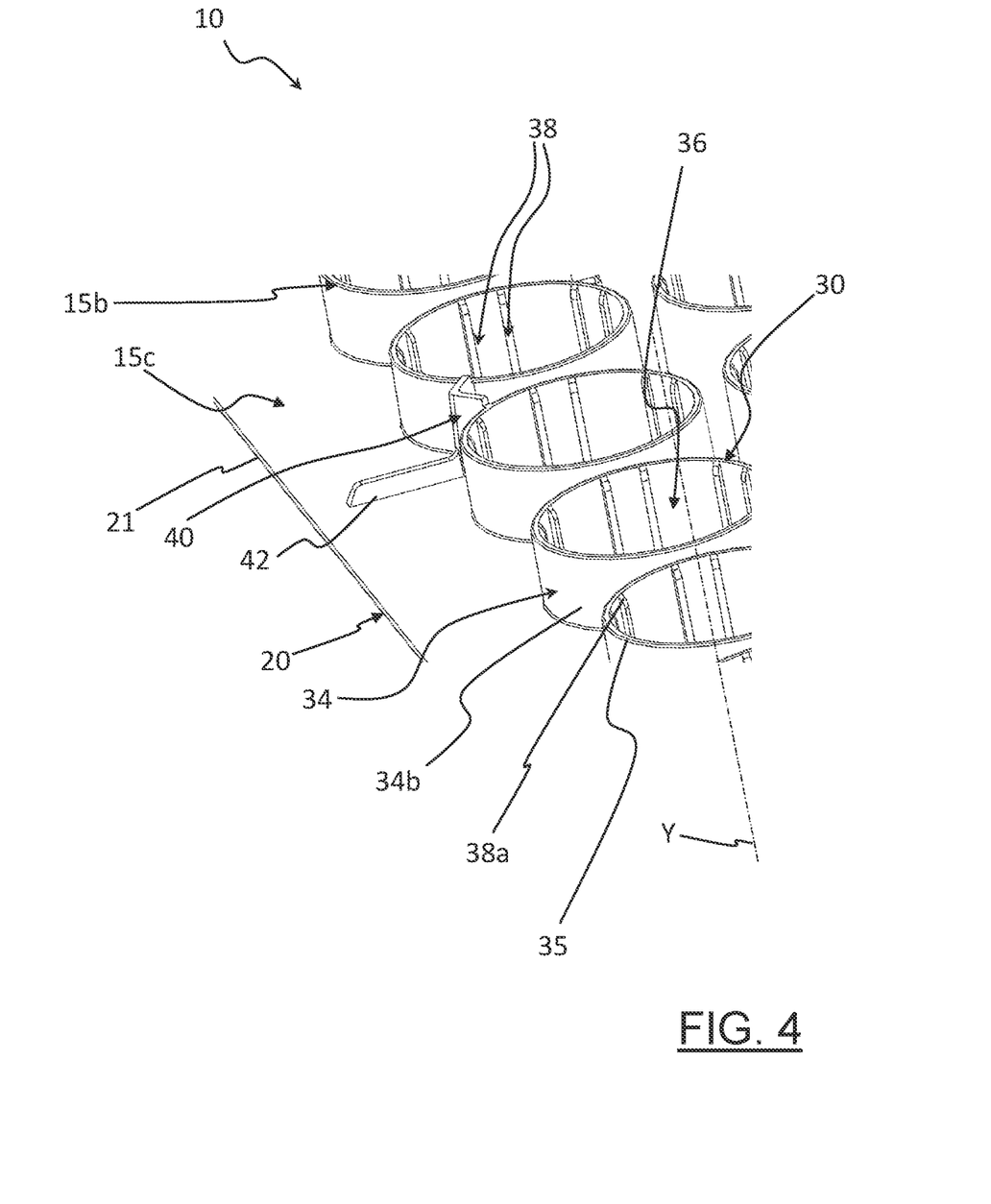
FIG. 4 is a schematic perspective view on an enlarged scale of a further portion of the support device of FIG. 1.

As shown for example in FIG. 3, the side walls 34 extend on opposite sides with respect to the plate 20. In this way, a lower portion 34a of the side wall 34 is placed below the plate 20 (i.e. on the side of the base 32) and an upper portion 34b of the side wall 34 is placed above the plate 20 (i.e. on the side of the upper end 31b).

In the non-limiting example of FIGS. 1-4, the base 32 is defined by six rest elements 32a projecting radially from the side wall 34 inwardly in the housing seat 30 and circumferentially equally spaced from each other, in particular arranged angularly offset by 60° from each other around the longitudinal axis Y. In other embodiments not shown, the rest elements are four and are angularly offset from each other by 90° or three and are angularly offset from each other by 120°.

In the present description and in the appended claims, the terms "axial" and the like are used to refer to a longitudinal direction of the housing seats 30 that is parallel to the longitudinal axis Y, the terms "radially" and the like are used to refer to any direction perpendicular to the abovementioned longitudinal axis Y, while the terms "circumferentially" and the like are used to refer to any circumferential direction about the abovementioned longitudinal axis Y.

Each rest element 32a has a quadrangular shape, substantially trapezoidal, and comprises a first side 32b connected to the side wall 34, a second side 32c arranged inside the housing seat 30 in a distal position with respect to the side wall 34 and preferably shorter than the first side 32b and two opposite third sides 32d connecting the first side 32b to the second side 32c.

To allow centering the cartridges within the respective housing seats 30, each housing seat 30 comprises a plurality of centering ribs 38 projecting radially from the tubular wall 34 inwardly in the housing seat 30 and extending along a longitudinal direction parallel to the longitudinal axis Y.

In the non-limiting example of FIGS. 1-4, the centering ribs 38 are twelve and have the same shape and dimensions as each other.

In general, the number of the centering ribs 38 is preferably even, so as to have a certain number of pairs of centering ribs 38, which in the non-limiting example of FIGS. 1-4 is six pairs.

Each pair of centering ribs 38 is arranged at and above a respective rest element 32a of the base 32.

The pairs of centering ribs 38 are circumferentially equally spaced from each other.

In the non-limiting example of FIGS. 1-4, the centering ribs 38 are arranged only above the rest elements 32a, so that in the circumferential spaces defined between pairs of adjacent rest elements 32a no centering ribs 38 are provided.

In particular, the centering ribs 38 of each pair of centering ribs 38 are arranged at the two third sides 32d of the respective rest element 32a.

In the non-limiting example of FIGS. 1-4, the centering ribs 38 extend on opposite sides with respect to the plate 20 between the rest elements 32a and the upper ends 31b of the housing seats 30.

Each centering rib 38 comprises, at a free end thereof that is distal from the respective rest element 32a, a tapered portion 38a configured to facilitate the insertion of the cartridge into the housing seat 30.

The support device 10 comprises a plurality of stacking elements 40 configured to allow stacking on the support device 10 another support device 10 of the same type.

In the non-limiting example of FIGS. 1-4, the stacking elements 40 are four and are arranged near two opposite sides 21 of the plate 20. The four stacking elements 40 are arranged substantially symmetrically with respect to a transverse centreline plane of the plate 20. In other embodiments that are not shown, the stacking elements 40 could be more or less than four, for example two or six.

Each stacking element 40 projects above the end edges 35 of the housing seats 30, and thus above the upper surface 15b.

In the non-limiting example of FIGS. 1-4, the stacking elements 40 are made in a single piece with the plate 20 and extend between the side walls 34 of two adjacent perimeter housing seats 30, in particular between the upper portions 34b of said two housing seats 30.

Each stacking element 40 is shaped like a "V", with the vertex of the "V" facing toward the perimeter edge 23.

Each stacking element 40 is connected, at the vertex of the "V", to a reinforcing rib 42 also arranged above the plate 20 and preferably made in a single piece with the stacking element 40 and the plate 20.

Further reinforcing ribs are arranged above the plate 20. In the non-limiting example of FIGS. 1-4, four further ribs 41 are arranged at the perimeter portion 15c, two of which are connected to the upper portions 34b of two perimeter housing seats 30. Further reinforcing ribs 41a are arranged at the central portion 15d between two respective adjacent housing seats 30.

Figure 2:
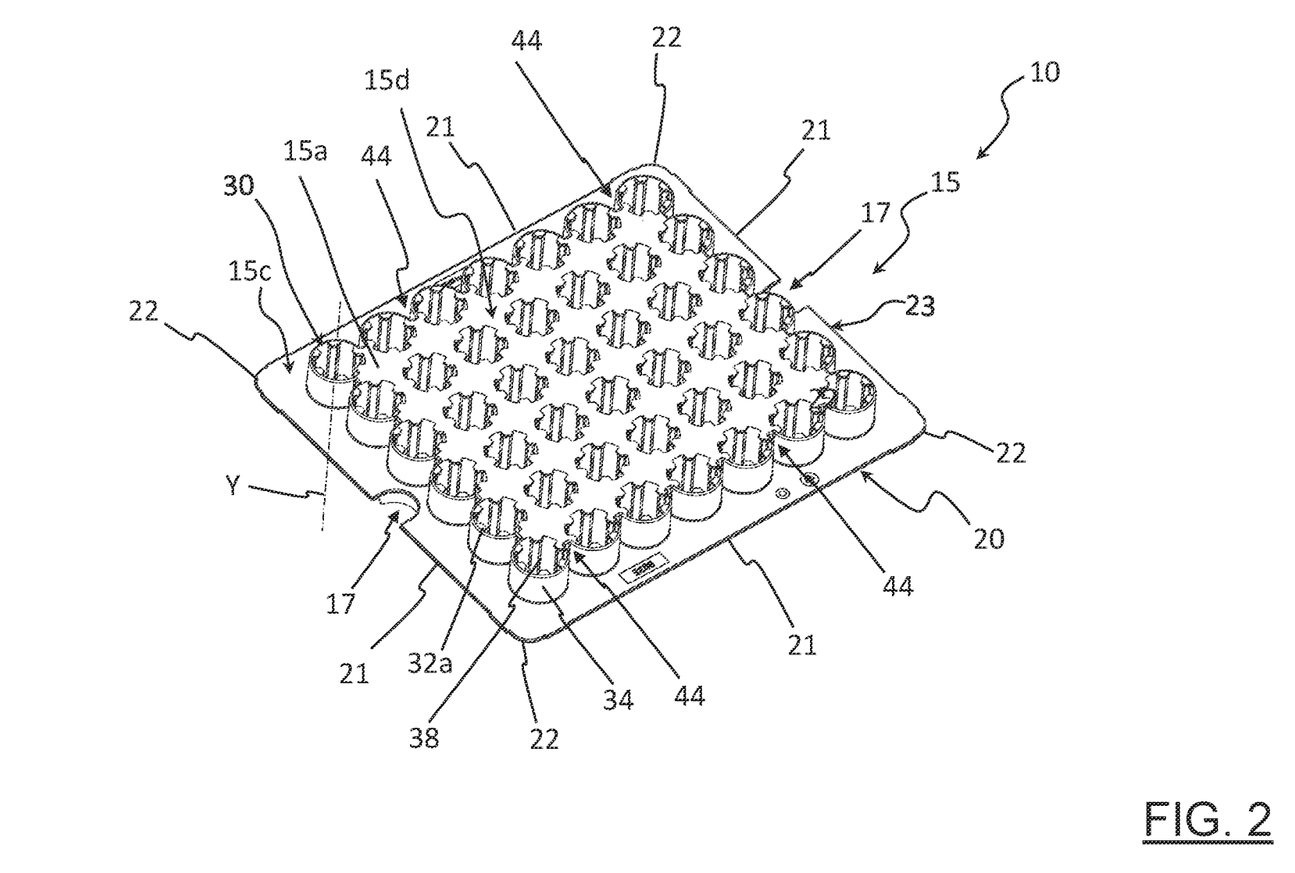
FIG. 2 is a schematic perspective bottom view of the support device of FIG. 1.

In the preferred embodiment illustrated herein, the plate 20 comprises, on the lower surface 15a, one or more recesses 44 formed between two respective adjacent housing seats 30 configured to house respective stacking elements of another support device 10 of the same type.

In particular, four recesses 44 are provided, each configured to house one of the abovementioned four stacking elements 40 (FIG. 2). Each recess 44 is defined between two lower portions 34a of the side walls 34 of two adjacent perimeter housing seats 30. The abovementioned recesses 44 are open towards the perimeter edge 23 of the plate 20.

The support device 10 described above can therefore be arranged both under another support device of identical type and over another support device of identical type, defining in both cases an assembly (or stack) of support devices which, thanks to the provision of stacking elements housed in respective recesses, is particularly stable.

Figure 5:
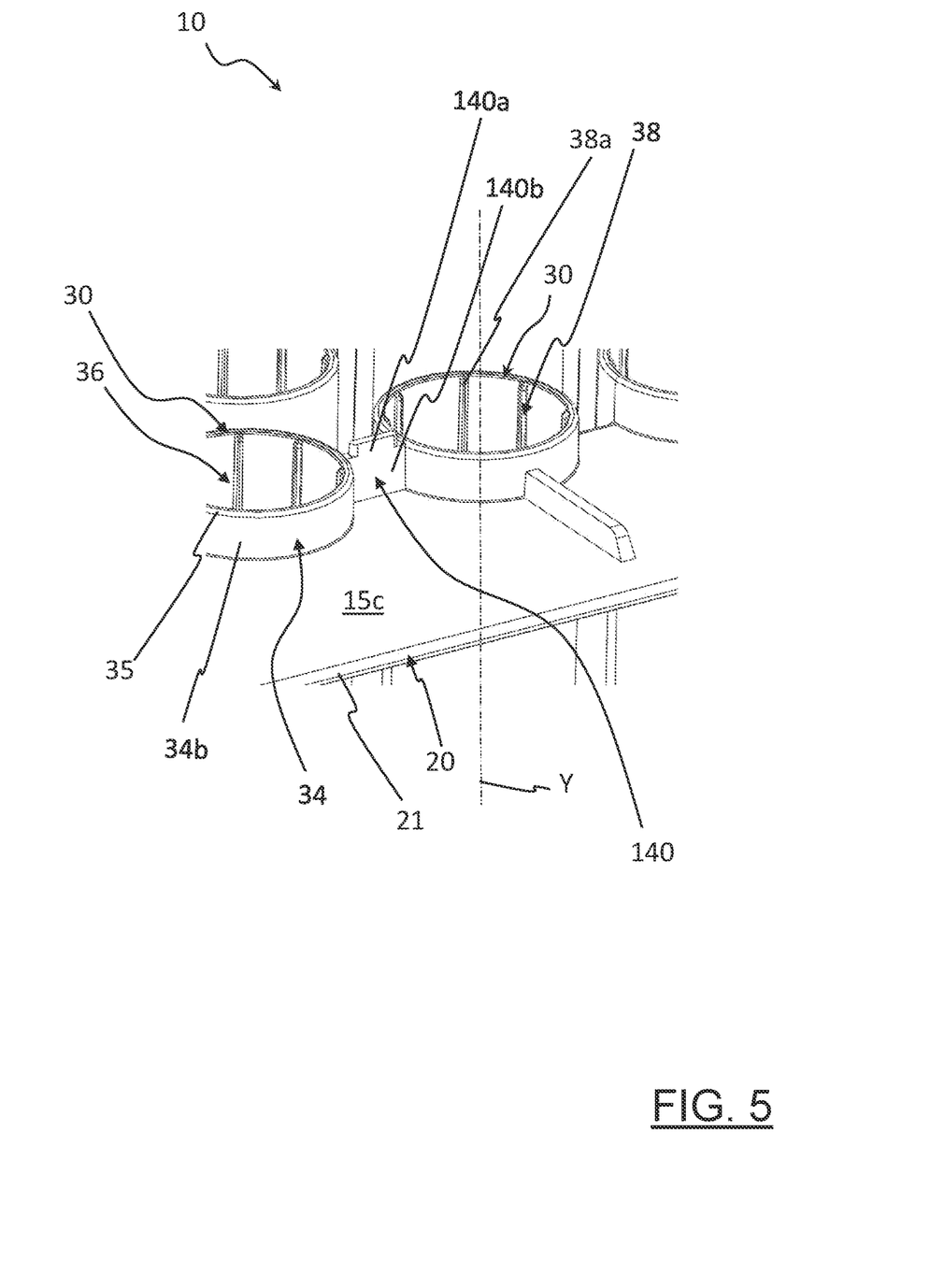
FIG. 5 is a schematic perspective view on an enlarged scale of a portion of a second embodiment of a support device in accordance with the present disclosure.

A second embodiment of a support device 10 in accordance with the present disclosure is shown in FIG. 5. Parts and components that are identical or analogous to those of the support device 10 of FIGS. 1-4 are indicated by the same reference numeral and for their description reference is made to the above description.

The support device 10 of FIG. 5 differs from the support device 10 of FIGS. 1-4 in the stacking elements, indicated with 140, which in this case have a cross-section shaped like an "I" and which do not have respective reinforcing ribs analogous to the reinforcing ribs 42 described above with reference to FIGS. 1-4.

Each stacking element 140 comprises an upper portion 140a projecting above the end edges 35 of the housing seats 30, and therefore above the upper surface 15b, and that has a transverse length, measured along a direction orthogonal to the longitudinal axis Y, which is lower than the distance between the two housing seats 30 connected by the stacking element 140. Said upper portion 140a extends from a lower portion 140b of the stacking element 140 that extends between the plate 20 and the end edges 35 and that connects the abovementioned two housing seats 30. The transverse length of the lower portion 140b is therefore greater than that of the upper portion 140a.

In the non-limiting example of FIG. 5, four pairs of centering ribs 38, arranged above four rest elements (not shown) are provided.

Figure 6:
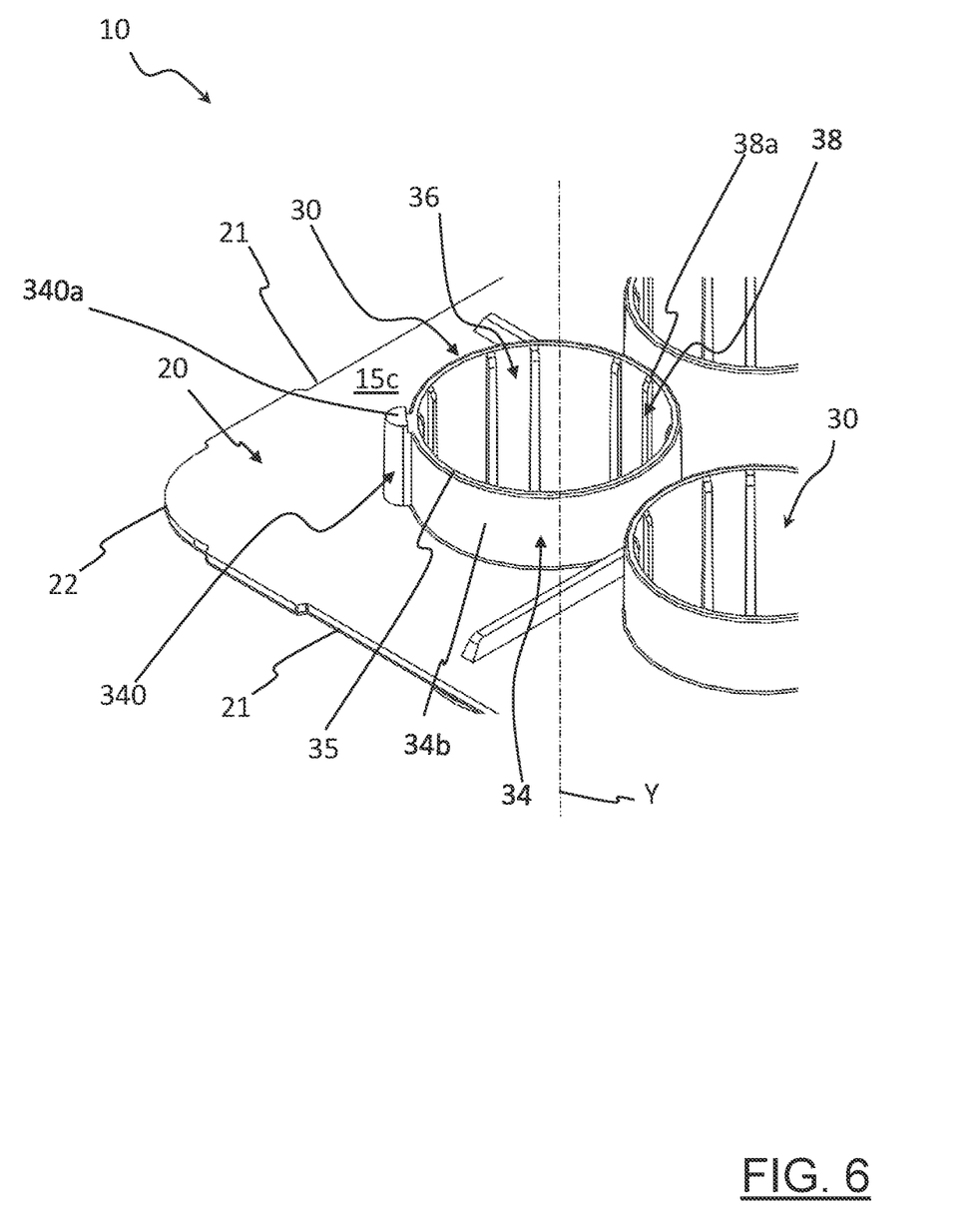
FIG. 6 is a schematic perspective view on an enlarged scale of a portion of a third embodiment of a support device in accordance with the present disclosure.

A third embodiment of a support device 10 in accordance with the present disclosure is shown in FIG. 6. Parts and components that are identical or analogous to those of the support device 10 of FIGS. 1-4 are indicated by the same reference numeral and for their description reference is made to the above description.

Looking at the plate 20 of the support device 10 of FIG. 6 from above, it can be noted that it differs from the support device 10 of FIGS. 1-4 in the stacking elements, that in this case are defined by stacking elements 340 extending outwardly from the upper portion 34b of the side wall 34.

Each of the stacking elements 340 comprises a respective upper portion 340a projecting above the end edges 35 of the housing seats 30.

In particular, in the embodiment of FIG. 6, each of the four perimeter housing seats 30 arranged at the four vertices 22 of the plate 20 comprises a respective stacking element 340 facing toward the perimeter portion 15c of the plate 20 and having a substantially semi-cylindrical shape.

Figure 7:
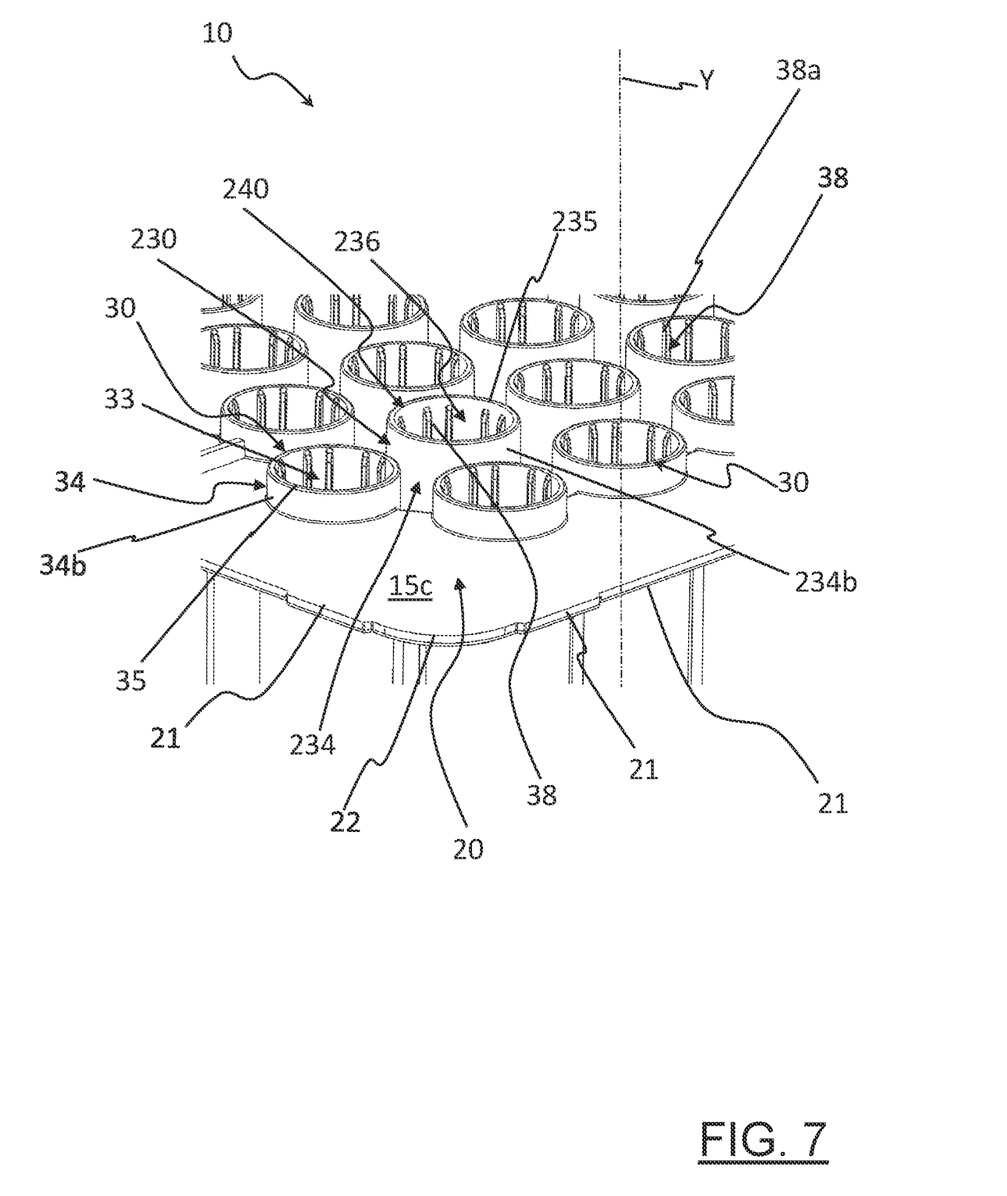
FIG. 7 is a schematic perspective view on an enlarged scale of a portion of a further embodiment of a support device in accordance with the present disclosure.
Figure 8:
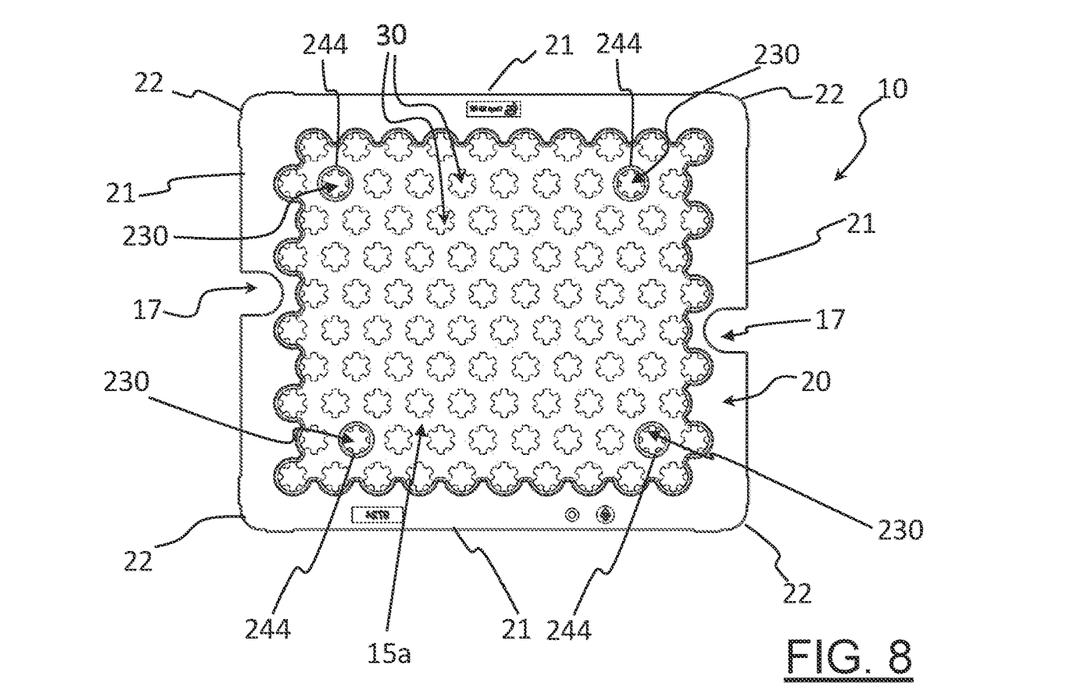
FIG. 8 is a plan bottom view of the support device of FIG. 7.
Figure 9:
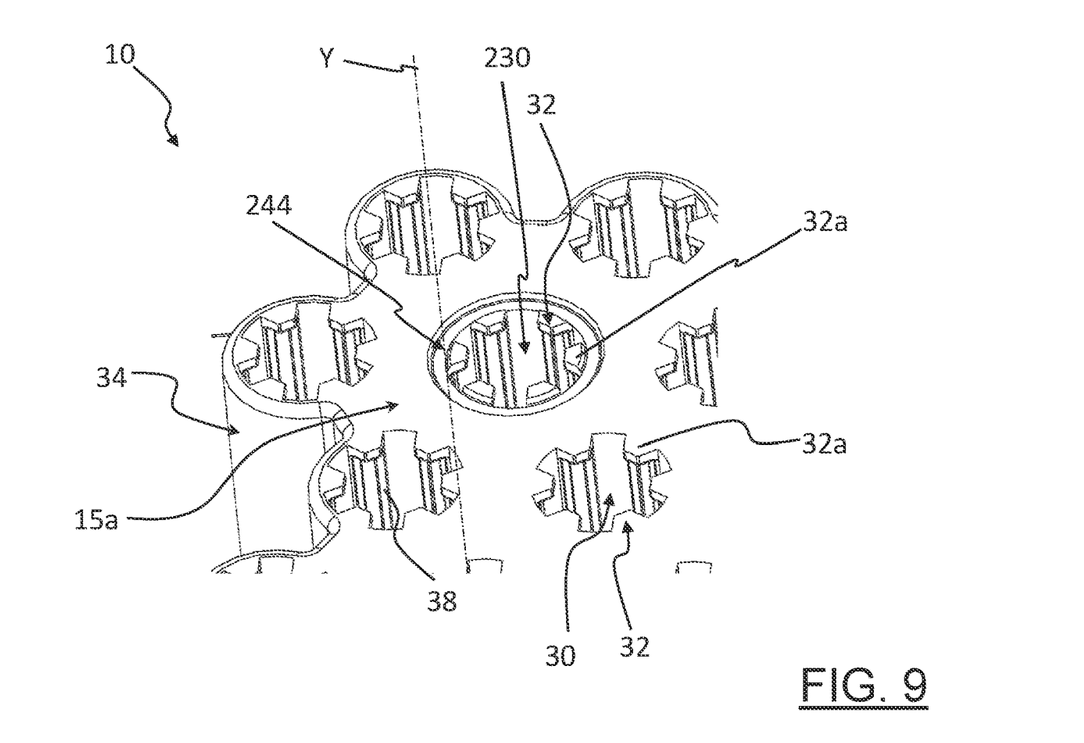
FIG. 9 is a schematic perspective view and on an enlarged scale of a portion of the support device of FIG. 8.

A further embodiment of a support device 10 in accordance with the present disclosure is shown in FIGS. 7-9. Parts and components that are identical or analogous to those of the support device of FIGS. 1-4 are indicated by the same reference numeral and for their description reference is made to the above description.

Looking at the plate 20 of the support device 10 of FIGS. 7-9 from above, it can be noted that it differs from the support device 10 of FIGS. 1-4 both in the arrangement of the housing seats 30, which in this case is staggered like a honeycomb or checkerboard, and in the stacking elements 240, which in this case are defined by end edges 235 of housing seats 230 projecting above the end edges 35 of the other housing seats 30 of the plate 20.

The housing seats 230 differ from the other adjacent housing seats 30 only in that their upper portion 234b of their side wall 234 has an extension greater than that of the upper portion 34b of the side wall 34 of the other housing seats 30.

The centering ribs 38 of the housing seats 230 are identical to the centering ribs 38 of the housing seats 30, whereby the centering ribs 38 of the housing seats 230 do not reach the end edges 235 of the housing seats 230.

The housing seats 230 are four, arranged near two opposite sides 21 of the plate 20 in a substantially symmetrical manner with respect to a transverse centreline plane of the plate 20.

Looking at the plate 20 of the support device 10 of FIGS. 7-9 from below, it can be noted that it differs from the support device 10 of FIGS. 1-4 also in that a plurality of annular-shaped recesses 244 are made on the lower surface 15a of the plate 20.

The recesses 244 are four and are arranged at the four housing seats 230.

Each recess 244 extends circumferentially around the base 32 of the respective housing seat 230.

Each base 32 of the housing seats 230 is identical to the base 32 of the housing seats 30 and comprises six rest elements 32a configured to support a respective cartridge. The lower face of the rest elements 32a of the housing seats 230 is defined on the lower surface 15a of the plate 20. The depth of the recesses 244 is lower than the thickness of the rest elements 32a.

The four recesses 244 are configured to house the end edges 235 of another support device 10 identical to that of FIGS. 7-9 so as to stack those two support devices 10.

Figure 10:
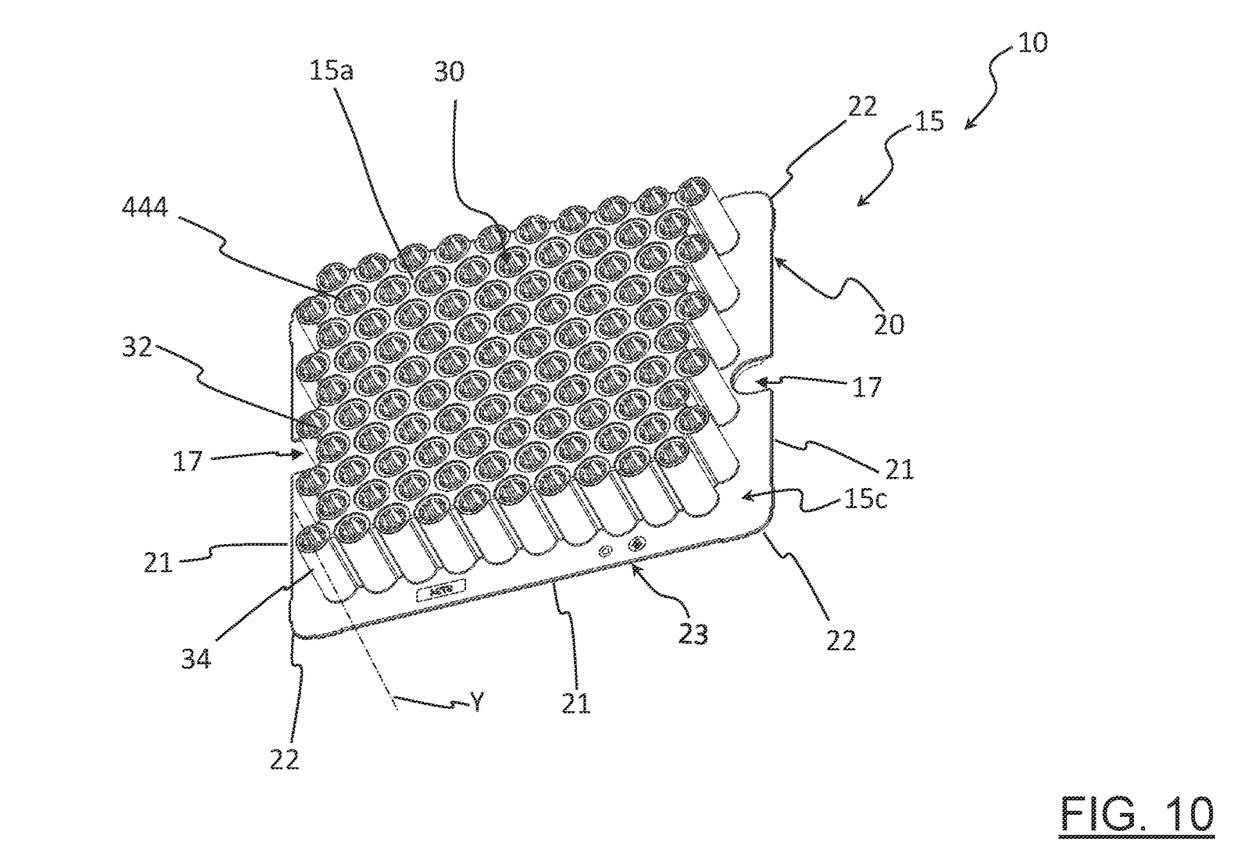
FIG. 10 is a schematic perspective bottom view of a support device.

A further embodiment of a support device 10 is shown in FIG. 10. Parts and components that are identical or analogous to those of the support device 10 of FIGS. 1-4 are indicated by the same reference numeral and for their description reference is made to the above description.

The support device 10 of FIG. 10 differs from the support device 10 of FIGS. 1-4 in that the stacking elements 40 are not provided and in that annular-shaped recesses 444 totally analogous to the recesses 244 of FIGS. 8 and 9 are made at all the housing seats 30.

Each base 32 of the housing seats 30 of FIG. 10 is identical to the base 32 of the housing seats 30 of FIGS. 1-4. Thus, the lower face of the base 32 of the housing seats 30 of FIG. 10 is defined on the lower surface 15a of the plate 20.

The recesses 444 are configured to house the end edges 35 of a support device 10 identical to that of FIG. 10 so as to stack said two support devices 10. The support device 10 provided with the abovementioned recesses 444 can therefore be arranged above or below another support device 10 of the same type.

The preferred embodiments of the disclosure have been described above to explain the principles of the present disclosure and its practical application to thereby enable others skilled in the art to utilize the present disclosure. However, as various modifications could be made in the constructions and methods herein described and illustrated without departing from the scope of the present disclosure, it is intended that all matter contained in the foregoing description or shown in the accompanying drawings, including all materials expressly incorporated by reference herein, shall be interpreted as illustrative rather than limiting. Thus, the breadth and scope of the present disclosure should not be limited by the above-described exemplary embodiment but should be defined only in accordance with the following claims appended hereto and their equivalents.

What is claimed is:

1. A support device for supporting a plurality of containers for pharmaceutical use to be handled in a processing line, comprising:
   a plate having a plurality of first housing seats, wherein each first housing seat comprises a first end edge protruding above the plate and defining an opening;
   a base within each first housing seat; and
   at least one stacking element protruding above the first end edges of the first housing seats; wherein
   i) said at least one stacking element connects two first adjacent housing seats, or
   ii) said at least one stacking element is defined by a second end edge of at least one second housing seat provided in the plate, said second end edge defining an opening for inserting a respective container into the second housing seat, or
   iii) said plate comprises a perimeter portion and a central portion delimited by the perimeter portion and said at least one stacking element comprises at least two stacking elements arranged at least two respective opposite vertices of the plate, said at least two respective opposite vertices being arranged at the perimeter portion of the plate.

2. The support device of claim 1, wherein the at least one stacking element is connected with the plate.

3. The support device according to option i) or iii) of claim 1, comprising four stacking elements arranged near two opposite sides of the plate.

4. The support device according to option i) of claim 1, wherein the two adjacent first housing seats are proximal to a perimeter edge of the plate.

5. The support device according to option i) of claim 1, wherein said at least one stacking element is shaped like one of a "V", a "I", or a "C" when viewing the support device from the above.

6. The support device according to option i) of claim 1, wherein the at least one stacking element is connected with a reinforcing rib arranged above the plate.

7. The support device according to option i) of claim 1, wherein the plate further comprises:
   a lower surface; and
   at least one recess formed between two adjacent housing seats and configured to house a respective stacking element of a further support device.

8. The support device according to option iii) of claim 1, wherein each second housing seat further comprises:
   at a lower end thereof, a second base configured to support the container within the second housing seat; and
   wherein the plate further comprises a recess on a lower surface of the plate, wherein the recess extends around the second base of the second housing seat.

* * * * *